United States Patent [19]

Rusin et al.

[11] Patent Number: 5,248,329
[45] Date of Patent: Sep. 28, 1993

[54] BIOLOGICAL PROCESSES FOR RECOVERING HEAVY METALS

[75] Inventors: Patricia A. Rusin; James E. Sharp, both of Tucson, Ariz.

[73] Assignee: Metallurgical and Biological Extraction Systems, Inc., Tucson, Ariz.

[21] Appl. No.: 23,990

[22] Filed: Feb. 26, 1993

Related U.S. Application Data

[63] Continuation-in-part of Ser. No. 828,056, Jan. 30, 1992, which is a continuation-in-part of Ser. No. 682,491, Apr. 9, 1991, abandoned, which is a continuation-in-part of Ser. No. 660,312, Feb. 22, 1991, abandoned.

[51] Int. Cl.$^5$ .............................................. C22B 11/04
[52] U.S. Cl. .............................. 75/715; 423/DIG. 17
[58] Field of Search .................. 75/715; 423/DIG. 17

[56] References Cited

U.S. PATENT DOCUMENTS 4,740,243  4/1988  Krebs-Yuill ................ 423/DIG. 17
4,752,332  6/1988  Wu .............................. 423/DIG. 17
4,765,827  8/1988  Clough et al. ........................ 423/21

OTHER PUBLICATIONS

Gupta, Asha and Henry L. Ehrlich (1989) "Selective and Non-Selective Bioleaching of Manganese from a Manganese-Containing Silver Ore" Journal of Biotechnology, 9:287–304.

*Primary Examiner*—Peter D. Rosenberg
*Attorney, Agent, or Firm*—Saliwanchik & Saliwanchik

[57] ABSTRACT

Disclosed is an efficient biological process for recovering heavy metals from refractory ore, and a process for removing heavy metal contaminants from the soil. The process utilizes a potato extract growth medium (PEGM) to greatly increase the efficiency for recovering heavy metals from ores and for removing heavy metal contaminants from soil. Microbes which can be used in the process are manganese reducing Bacillus sp., or mutants thereof which retain the metal recovering properties of the parent microbe. Further, recombinant microbes, as disclosed herein, can be used in the same manner as the native microbe.

12 Claims, No Drawings

BIOLOGICAL PROCESSES FOR RECOVERING HEAVY METALS

CROSS-REFERENCE TO A RELATED APPLICATION

This is a continuation-in-part of pending application Ser. No. 07/828,056, filed Jan. 30, 1992, which is a continuation-in-part of application Ser. No. 07/682,491, filed on Apr. 9, 1991, now abandoned, which was a continuation-in-part of application Ser. No. 07/660,312, filed on Feb. 22, 1991, now abandoned.

BACKGROUND OF THE INVENTION

The recovery of metals from ore is made more difficult by the presence of other metals in the ore. Chemical processes for recovery of precious metals are disclosed in U.S. Pat. Nos. 4,740,243, 4,752,332, and 4,765,827. None of these patents disclose processes which come close to the recovery efficiency for metals achieved with the subject invention process.

Biological recovery of silver and manganese from refractory ore is disclosed in Gupta, A., and H. L. Ehrlich in Jour. of Biotechnology (1989) 9: 287–304. Disclosed is the use of a mold, Penicillium, incubated aerobically, without a chelator with the ore. After 5 weeks incubation, a 23.5% solubilization of Mn and 26.5% solubilization of silver was achieved. This result is not considered to be an efficient silver or manganese recovery.

Soils contaminated with heavy metals, e.g., plutonium, uranium, and the like, pose severe health problems to humans and animals. Thus, the removal of these heavy metal contaminates is a desirable goal. The subject biological process accomplishes this desirable goal.

BRIEF SUMMARY OF THE INVENTION

The subject invention concerns the use of a Potato Extract Growth Medium (PEGM), as disclosed herein, to recover metals from various ores and also to bioremediate soils contaminated with undesired metals. Examples of heavy metals which can be removed from contaminated soils by the processes of the subject invention are plutonium, uranium, copper, silver, gold, manganese, iron, zinc, lead, arsenic, americium, gallium, germanium, chromium, nickel, thorium, tellurium, molybdenum, tin, cadmium, mercury, cobalt and the like.

Any of the microbes disclosed in U.S. Pat. No. 5,055,130 (Bacillus polymyxa) and the microbes disclosed in U.S. application Ser. No. 07/828,056 (Bacillus MBX69, mutants thereof, or any manganese reducing Bacillus sp.) can be used in the subject process to efficiently recover metals from ores or decontaminate soils as disclosed herein. Further, the process of the subject invention can be used with mutants of these microbes so long as the mutants retain the biological property of the parent in the recovery of metals from ores and soil. Still further, recombinant microbes, as disclosed herein, can be used in the subject process.

DETAILED DISCLOSURE OF THE INVENTION

Upon contacting mined ore, e.g., manganiferous silver oxide ore, with a culture of the microbe grown in PEGM, as defined herein, there is obtained a liquid portion containing the desired metal. The desired metal can be removed from the liquid portion by standard procedures. For example, if the desired metal is silver, it can be processed in a standard manner through cyanide extraction and the silver recovered using standard metallurgical techniques. See Mineral Processing Technology, 1988, 4th ed. by B. A. Wills, Pergomon Press, New York. Preferably, the invention process is conducted under substantially anaerobic conditions.

Microbes which can be used in the subject process are manganese reducing Bacillus sp. Manganese reducing Bacillus sp. can be isolated by the following procedure:

Obtain samples of ore of interest and of sediments or water near ore deposit site. Make dilutions of samples in a standard mineral salts medium comprising $MnO_2$. Incubate tubes at about room temperature and examine for Mn reduction. Isolate Mn reducers on solid agar plates and reconfirm Mn reduction in same medium as used for initial isolation.

IDENTIFICATION

Perform gram stain of bacterium. Biochemical tests are done and identification is according to Bergey's Manual of Determinative Bacteriology.

COMPARATIVE MN REDUCTION KINETICS

Combine growth medium, test bacterium and ore in test tube. Incubate with agitation for 2–7 days at room temperature. Analysis for solubilized Mn is performed with a standard calorimetric method, or standard atomic absorption (AA). After incubation at room temperature, add excess cyanide to tube, agitate for 24–48 hrs and analyze supernatant for solubilized silver. Choose bacterium which solubilizes the most manganese and silver.

The PEGM of the subject invention has the following composition: Starting material (Raw potato)

|  | Fresh |  | Range |
|---|---|---|---|
| Water | 77% |  | 69–85% |
| Ash | 1% |  | 0.08–1.2% |
| Protein | 2.5% |  | 2.0–3.0% |
| Fat | 0.1% |  | 0.08–0.13% |
| Fiber | 0.4% |  | 0.2–0.6% |
| Carbohydrate | 20.3% |  | 18–22% |
| Total Carbon | 9% |  | 8–10% |
| Starch | 18% |  | 16–20% |
| Glucose | 0.5% |  | 0.4–0.6% |
| Vitamin A | trace |  | trace |
| Ascorbic Acid | 200 | mg/kg (0.02%) | 0.01–0.03% |
| Niacin | 15 | mg/kg (0.0015%) | 0.0012–0.0010% |
| Thiamine | 1.0 | mg/kg (0.0001%) | 0.00005–0.0003% |
| Riboflavin | 0.4 | mg/kg (0.00004%) | 0.00002–0.00006% |
| Iron | 0.001% |  | 0.01–0.0005% |
| Phosphorus | 0.05% |  | 0.02–0.08% |
| Potassium | 0.41% |  | 0.2–0.6% |
| Sodium | 0.02% |  | 0.01–0.03% |
| Chlorine | 0.07% |  | 0.05–0.1% |
| Copper | 4.1 | mg/kg (0.00041%) | 0.0002–0.0006% |
| Magnesium | 0.03% |  | 0.02–0.04% |
| Manganese | 9.6 | mg/kg (0.00096%) | 0.0007–0.002% |
| Calcium | 0.01% |  | 0.05–0.02% |
| Sulfur | 0.02% |  | 0.01–0.03% |

Potatoes are cut up and heated in the presence of water. The potato extract may be diluted. However, the relative percentages of constituents shown above remains the same.

PEGM is used as a microbial growth medium. Bacteria are inoculated into the medium and incubated until $\geq 10^6$ bacteria. The bacterial culture is contacted with ore for a sufficient length of time to extract metals. Ore may be contacted with the growth medium at the time of bacterial inoculation if desired.

The potato extract may also be used as an additive to mine leach solution. A range of 5-25% of the leach solution may be comprised of PEGM.

Bacteria use the carbohydrates (primarily starch and glucose) as sources of carbon. Protein is used as both a carbon source and a nitrogen source. The other constituents are important growth factors to the bacteria. The carbohydrates are also used as an energy source by the bacteria. The nutrients are necessary for bacterial growth. Energy is necessary for bacterial growth and for the solubilization of metals. The bacteria obtain energy from PEGM enabling them to act as a catalyst in electron transfer reactions resulting in the oxidation or reduction of minerals. The oxidation or reduction of minerals is necessary to solubilize metals.

The constituents in PEGM are converted by the bacteria to metabolic endproducts including carbon dioxide, water, ammonium, acetic acid, lactic acids, butyric acid, isobutyric acid, pyruvic acid, valeric acid, isovaleric acid, propionic acid, acetone, and other organic acids. The bacterial products include alpha ketoglutarate, succinic acid, malic acid, citric acid, and other products from the citric acid cycle.

Recombinant microbes, which can be used in the invention process, can be made by isolating the gene(s) from the microbes disclosed herein, and transforming suitable hosts with the gene(s). The gene(s) encode enzymes which are capable of solubilizing metal contaminants found in refractory ore, e.g., silver ore. These recombinant microbes can be used in the same manner as the parent microbes, as disclosed herein, to recover metals from ores and soil.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing Microbes in Potato Extract Growth Medium (PEGM)

Microbial cultures comprising PEGM and microbes, as disclosed herein, have been contacted with oxide ores for the purpose of extracting metals. After 6-14 days contact, the following extractions have been achieved: copper, 99%; manganese 98%, lead, 70%; zinc, 80%; silver, 86%; iron, 60%; and molybdenum, 93%.

PEGM has also been used as an additive to mine leach solution for sulfide ores. The addition of PEGM to the leach solution resulted in 15-25% increased copper extraction over that achieved by unmodified leach solution.

The PEGM can be sterilized in standard flasks, which are then subsequently inoculated with the desired microbe. These flasks can be inoculated at about 30° C. on a rotary shaker at about 200 rpm for about 64 hours. If desired, a chelator, e.g., nitrilotriacetic acid and the like, can be added to the medium to facilitate metal recovery. As disclosed above, the various metals can be recovered from the liquid culture portion by standard procedures.

The above media and procedures can be readily scaled up to large fermentors by procedures well known in the art.

EXAMPLE 2

Biotreatment of Mined Silver Ore

Mined silver ore and a bacterial culture grown in PEGM of a manganese reducing Bacillus sp., e.g., Bacillus MBX 69, are combined in a bioreactor. The bacteria-ore mixture is incubated at a temperature of about 27° C. with agitation while slowly percolating with nitrogen gas if necessary to maintain anaerobic conditions. Retention time in the bioreactor will vary with the ore used and will be from about 2 to about 6 days. With some ore samples, the bacterial culture will need to be replaced with a 50-100% turnover daily. The liquid bacterial culture then can be separated from the residual ore by standard procedures. Soluble silver, manganese, plutonium, uranium, and other metals, as disclosed herein, can be chemically stripped from the liquid portion by standard procedures. The residual ore is subject to a standard cyanidation process, and residual silver is recovered through standard metallurgical techniques.

Alternatively, the desired metals can be recovered from the residue and/or liquid portion of a culture or enzyme reaction without first separating the components.

EXAMPLE 3

Remediation of Soil Contaminated with Metals

Soil contaminated with metals, as disclosed herein, can be treated in a bioreactor, as described in Example 2, or by other bioreactors known in the art, to remove the metal contaminants. Such bioreactors can be batch type or continuous fermentation types. These technologies are well known to a person skilled in the art of bioremediation. Alternatively, active cultures of the invention microbe, or gene(s) therefrom, can be contacted with the contaminated soil in situ. Preferably, the leaching of the heavy metals, e.g., plutonium, from contaminated soils is done with the bioreductive bacterium and a chelator, as disclosed herein.

EXAMPLE 4

Remediation of Soil with *Bacillus polymyxa*

The microbe disclosed in U.S. Pat. No. 5,055,130, *Bacillus polymyxa*, can be used in place of Bacillus MBX 69 in Example 3 to recover heavy metals, as disclosed herein, from soils contaminated with such.

We claim:

1. A process for recovering heavy metals from refractory ore which comprises (a) culturing a manganese reducing Bacillus species in potato extract growth medium, (b) contacting said ore with the culture of (a) for a sufficient time to solubilize heavy metals in said ore to obtain a residue and a liquid portion; and (c) recovering said metals from said liquid portion.

2. The process, according to claim 1, wherein said potato extract growth medium has the following composition:

| | Range |
|---|---|
| Water | 69-85% |
| Ash | 0.08-1.2% |
| Protein | 2.0-3.0% |
| Fat | 0.08-0.13% |
| Fiber | 0.2-0.6% |
| Carbohydrate | 18-22% |
| Total Carbon | 8-10% |
| Starch | 16-20% |
| Glucose | 0.4-0.6% |
| Vitamin A | trace |
| Ascorbic Acid | 0.01-0.03% |
| Niacin | 0.0012-0.0010% |

-continued

|  | Range |
| --- | --- |
| Thiamine | 0.00005–0.0003% |
| Riboflavin | 0.00002–0.00006% |
| Iron | 0.01–0.0005% |
| Phosphorus | 0.02–0.08% |
| Potassium | 0.2–0.6% |
| Sodium | 0.01–0.03% |
| Chlorine | 0.05–0.1% |
| Copper | 0.0002–0.0006% |
| Magnesium | 0.02–0.04% |
| Manganese | 0.0007–0.002% |
| Calcium | 0.05–0.02% |
| Sulfur | 0.01–0.03% |

3. The process, according to claim 1, wherein said potato extract growth medium has the following composition:

|  | Fresh |  |
| --- | --- | --- |
| Water | 77% |  |
| Ash | 1% |  |
| Protein | 2.5% |  |
| Fat | 0.1% |  |
| Fiber | 0.4% |  |
| Carbohydrate | 20.3% |  |
| Total Carbon | 9% |  |
| Starch | 18% |  |
| Glucose | 0.5% |  |
| Vitamin A | trace |  |
| Ascorbic Acid | 200 | mg/kg (0.02%) |
| Niacin | 15 | mg/kg (0.0015%) |
| Thiamine | 1.0 | mg/kg (0.0001%) |
| Riboflavin | 0.4 | mg/kg (0.00004%) |
| Iron | 0.001% |  |
| Phosphorus | 0.05% |  |
| Potassium | 0.41% |  |
| Sodium | 0.02% |  |
| Chlorine | 0.07% |  |
| Copper | 4.1 | mg/kg (0.00041%) |
| Magnesium | 0.03% |  |
| Manganese | 9.6 | mg/kg (0.00096%) |
| Calcium | 0.01% |  |
| Sulfur | 0.02% |  |

4. The process, according to claim 1, wherein said Bacillus species is Bacillus MBX 69, having the identifying characteristics of NRRL B-18768, or mutants thereof.

5. The process, according to claim 1, wherein said heavy metals are selected from the group consisting of copper, silver, gold, manganese, iron, zinc, lead arsenic, americium, gallium, germanium, chromium, nickel, uranium, plutonium, thorium, tellurium, molybdenum, tin, cadmium, mercury and cobalt.

6. A process for removing heavy metals from soil which comprises (a) culturing a manganese reducing Bacillus species in potato extract growth medium; (b) contacting said soil with the culture of (a) for a sufficient time to solubilize heavy metals in said soil to obtain a residue and a liquid portion; and (c) recovering the heavy metals from said liquid portion.

7. The process, according to claim 6, wherein said potato extract growth medium has the following composition:

|  | Range |
| --- | --- |
| Water | 69–85% |
| Ash | 0.08–1.2% |
| Protein | 2.0–3.0% |
| Fat | 0.08–0.13% |
| Fiber | 0.2–0.6% |
| Carbohydrate | 18–22% |
| Total Carbon | 8–10% |
| Starch | 16–20% |
| Glucose | 0.4–0.6% |
| Vitamin A | trace |
| Ascorbic Acid | 0.01–0.03% |
| Niacin | 0.0012–0.0010% |
| Thiamine | 0.00005–0.0003% |
| Riboflavin | 0.00002–0.00006% |
| Iron | 0.01–0.0005% |
| Phosphorus | 0.02–0.08% |
| Potassium | 0.2–0.6% |
| Sodium | 0.01–0.03% |
| Chlorine | 0.05–0.1% |
| Copper | 0.0002–0.0006% |
| Magnesium | 0.02–0.04% |
| Manganese | 0.0007–0.002% |
| Calcium | 0.05–0.02% |
| Sulfur | 0.01–0.03% |

8. The process, according to claim 6, wherein said potato extract growth medium has the following composition:

|  | Fresh |  |
| --- | --- | --- |
| Water | 77% |  |
| Ash | 1% |  |
| Protein | 2.5% |  |
| Fat | 0.1% |  |
| Fiber | 0.4% |  |
| Carbohydrate | 20.3% |  |
| Total Carbon | 9% |  |
| Starch | 18% |  |
| Glucose | 0.5% |  |
| Vitamin A | trace |  |
| Ascorbic Acid | 200 | mg/kg (0.02%) |
| Niacin | 15 | mg/kg (0.0015%) |
| Thiamine | 1.0 | mg/kg (0.0001%) |
| Riboflavin | 0.4 | mg/kg (0.00004%) |
| Iron | 0.001% |  |
| Phosphorus | 0.05% |  |
| Potassium | 0.41% |  |
| Sodium | 0.02% |  |
| Chlorine | 0.07% |  |
| Copper | 4.1 | mg/kg (0.00041%) |
| Magnesium | 0.03% |  |
| Manganese | 9.6 | mg/kg (0.00096%) |
| Calcium | 0.01% |  |
| Sulfur | 0.02% |  |

9. The process, according to claim 6, wherein a chelating agent is present in the growth medium.

10. The process, according to claim 6, wherein said Bacillus species is a manganese-reducing *Bacillus polymyxa* bacteria.

11. The process, according to claim 10, wherein said *Bacillus polymyxa* is *Bacillus polymyxa* strain D-1, having the identifying characteristics of ATCC-55030, or mutants thereof.

12. The process, according to claim 6, wherein said heavy metal is selected from the group consisting of copper, silver, gold, manganese, iron, zinc, lead arsenic, americium, gallium, germanium, chromium, nickel, uranium, plutonium, thorium, tellurium, molybdenum, tin, cadmium, mercury and cobalt.

* * * * *

UNITED STATES PATENT AND TRADEMARK OFFICE
CERTIFICATE OF CORRECTION

PATENT NO. : 5,248,329
DATED : September 28, 1993
INVENTOR(S) : Patricia A. Rusin and James E. Sharp It is certified that error appears in the above-indentified patent and that said Letters Patent is hereby corrected as shown below:

Column 5, line 12: Delete "0.0007" and insert therefor --0.007--.

Column 6, line 21: Delete "0.0007" and insert therefor --0.007--.

Signed and Sealed this

Tenth Day of May, 1994

Attest:

BRUCE LEHMAN

Attesting Officer     Commissioner of Patents and Trademarks